(12) United States Patent
Dittmer et al.

(10) Patent No.: US 10,151,750 B2
(45) Date of Patent: Dec. 11, 2018

(54) MAGNETIC AND/OR ELECTRIC LABEL ASSISTED DETECTION SYSTEM AND METHOD

(71) Applicant: KONINKLIJKE PHILIPS N.V., Eindhoven (NL)

(72) Inventors: Wendy Uyen Dittmer, Eindhoven (NL); Menno Willem Jose Prims, Rosmalen (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1017 days.

(21) Appl. No.: 14/570,381

(22) Filed: Dec. 15, 2014

(65) Prior Publication Data

US 2015/0104784 A1 Apr. 16, 2015

Related U.S. Application Data

(62) Division of application No. 12/444,698, filed as application No. PCT/IB2007/054055 on Oct. 5, 2007, now Pat. No. 8,936,932.

(30) Foreign Application Priority Data

Oct. 12, 2006 (EP) .................... 06122177

(51) Int. Cl.
*G01N 33/00* (2006.01)
*G01N 33/543* (2006.01)
*G01N 27/74* (2006.01)
*G01N 35/00* (2006.01)

(52) U.S. Cl.
CPC ..... *G01N 33/54326* (2013.01); *G01N 27/745* (2013.01); *G01N 35/0098* (2013.01)

(58) Field of Classification Search
None
See application file for complete search history.

(56) References Cited

U.S. PATENT DOCUMENTS

| | | | |
|---|---|---|---|
| 4,756,884 A | 7/1988 | Allen | |
| 6,548,311 B1* | 4/2003 | Knoll | C12Q 1/6825 205/777.5 |
| 6,709,633 B2 | 3/2004 | Etes | |
| 7,106,051 B2 | 9/2006 | Prins | |
| 7,425,253 B2 | 9/2008 | Voldman | |

(Continued)

FOREIGN PATENT DOCUMENTS

| | | |
|---|---|---|
| JP | 3262869 A | 11/1991 |
| WO | 2000079276 A1 | 12/2000 |

(Continued)

OTHER PUBLICATIONS

Collins English Dictionary (2003)

*Primary Examiner* — Melanie Yu Brown
*Assistant Examiner* — Richard Moerschell

(57) ABSTRACT

A detection method (200) detects analytes in a fluid sample. The detection method includes transporting magnetic and/or electric labels (5) after interaction between the sample fluid and a reagent towards a detection receptacle (1). The detection receptacle (1) is initially substantially magnetic and/or electric label (5) free. By transporting the magnetic and/or electric labels (5) after reaction, interference between unreacted reagents and magnetic and/or electric label-assisted detection can be reduced.

9 Claims, 7 Drawing Sheets

(56) References Cited

U.S. PATENT DOCUMENTS

| | | |
|---|---|---|
| 2001/0034068 A1 | 10/2001 | Spivey |
| 2002/0009389 A1 | 1/2002 | Lappe |
| 2002/0022276 A1 | 2/2002 | Zhou |
| 2002/0042145 A1 | 4/2002 | Forsberg |
| 2004/0043511 A1 | 3/2004 | Chen |
| 2004/0214347 A1 | 10/2004 | LaBorde |
| 2005/0175981 A1 | 8/2005 | Voldman |
| 2005/0244987 A1 | 11/2005 | Utsunomiya |
| 2006/0008896 A1* | 1/2006 | Nazareth ............ G01N 21/8483 435/287.2 |
| 2006/0011552 A1 | 1/2006 | Utsunomiya |
| 2006/0081954 A1 | 4/2006 | Tondra |
| 2006/0257956 A1 | 11/2006 | Basset |
| 2007/0074972 A1* | 4/2007 | Nassef .............. B01L 3/502738 204/451 |
| 2008/0226500 A1 | 9/2008 | Honda |
| 2009/0071831 A1 | 3/2009 | Chen |

FOREIGN PATENT DOCUMENTS

| | | | |
|---|---|---|---|
| WO | 2000079278 A1 | 12/2000 | |
| WO | WO 01/01025 * | 1/2001 | ............ F16K 17/00 |
| WO | 2003054523 A2 | 7/2003 | |
| WO | 2004011942 A1 | 2/2004 | |
| WO | 2006134546 A2 | 12/2006 | |

\* cited by examiner

MAGNETIC AND/OR ELECTRIC LABEL ASSISTED DETECTION SYSTEM AND METHOD

CROSS REFERENCE TO PRIOR APPLICATIONS

This application is a Divisional application of U.S. application Ser. No. 12/444,698, filed on Apr. 8, 2009, which is the U.S. National Phase Application of International Application No. PCT/IB2007/054055, filed on Oct. 5, 2007 and claims the benefit of European Patent Application No. 06122177.6, filed on Oct. 12, 2006. These application are hereby incorporated by reference herein.

FIELD OF THE INVENTION

The present invention relates to the field of sensors especially biosensors. More particularly, the present invention relates to methods and systems for detecting analytes, e.g. as used in qualitative or quantitative detection of biological, chemical or bio-chemical compounds, and to means for improving such detection methods and systems.

BACKGROUND OF THE INVENTION

Biosensors typically are devices that allow qualitatively or quantitatively detection of target molecules, also called "analytes", such as e.g. proteins, cells, viruses, bacteria, protozoa, cell components, cell membranes, spores, DNA, RNA, etc. in a liquid, such as for example blood, serum, plasma, urine, saliva, tissue extract, interstitial fluid, cell-culture extract, food or feed extract, liquids such as drinking water, etc. One of the measuring principles is the counting of labelled molecules attached at predetermined sites on the biosensor. For example, the molecules may be labelled with magnetic particles or beads and these magnetic particles or beads can be detected with a magnetic sensor. Alternatively, the amount of analyte may be detected by optical methods such as fluorescence. In this case the analyte itself may carry a fluorescent label, or alternatively an additional incubation with a fluorescent labelled second recognition element may be performed. Some molecules to be analysed are self-fluorescent.

There are a number of label-based assays used in the analytical detection of a target. These include the sandwich, competitive and inhibition assays. In some formats for these assays the assay reaction must be separated in time from the detection of the label. In some assays it is desirable to first complete the assay reaction on the sensor surface and thereafter attach the label for detection. This sequence of reactions is often used for immunoassays in which a sandwich of the target between a primary and secondary antibody is first formed on the surface, e.g. using a biotinylated secondary antibody, and thereafter the label, e.g. containing streptavidin, is bound to the sensor through the sandwich. In other assays it is more effective to first complete the assay reaction on the label and then bring the label to the sensor for detection. Examples include the assays based on a strong-binding couple for the attachment of the label to the sensor surface. In this assay, a sandwich of the target between a primary and secondary antibody is first formed on the label and thereafter the label is bound on the sensor surface for detection. In such assays, it is desirable to prevent the unreacted reagents (e.g. reagents that have not reacted to form a sandwich) from binding to the label or sensor surface and then blocking the label from being detected. Methods for doing this include removing the reagents by washing the reaction vessel or binding them onto a reactive, non-sensor surface. Washing is inconvenient as it involves extra fluid handling steps and can also result in the removal of the labels to be detected. It is also difficult to avoid that the label also binds to the reactive surface intended for unreacted reagents.

Magnetic biosensors detect biological targets labeled with magnetic particles. US 2006/0011552 A1 discloses an apparatus and method for separating a predetermined amount of magnetic particles in a fluid. In the system, magnetic particles from a fluid are captured at a fluid conveyance portion. The latter is performed using a magnetic field at the fluid conveyance portion positioned at a cross-section of a fluid supply channel and a discharge channel. Thereafter, the magnetic particles are discharged by a way of a medium introduced into the second flow channel. In this way, a predetermined amount of magnetic particles is provided in a fluid.

SUMMARY OF THE INVENTION

An object of the present invention is to obtain good methods, apparatus and systems for detecting biological, chemical and/or bio-chemical particles. The above objective is accomplished by devices and a method according to the present invention.

The invention relates to a detection system prepared for detecting at least one target molecule, the detection system comprising at least a first receptacle comprising a detection surface, the at least a first receptacle being substantially free of magnetic and/or electric labels prior to use, at least a second receptacle comprising, prior to use, at least one magnetic and/or electric label for enabling magnetic and/or electric label assisted detection, the at least one magnetic and/or electric label being adapted for interacting with the at least one target molecule, and a magnetic and/or electric field generator for enabling transport of the at least one magnetic and/or electric label from at least the second receptacle to at least the first receptacle, thereby enabling detection of a magnetic and/or electric label assisted detection signal. It is an advantage of embodiments according to the present invention that the assay reactions involving a target or target homologue are separated in time from detection of the magnetic and/or electric label by the sensor. It is an advantage of embodiments according to the present invention that bulk fluid actuation steps may be minimized, as e.g. the number and/or strength of rinsing steps can be reduced compared to prior art systems, e.g. preferably not more than one unidirectional bulk-fluid actuation step is performed. It is also an advantage of some embodiments that unreacted reagents can be hindered from entering the detection receptacle. The magnetic and/or electric label may be a magnetic label, e.g. assisting in magnetic label assisted detection.

The detection system may be adapted for enabling a fluid flow from the at least a first receptacle to the at least a second receptacle. The magnetic and/or electric field generator may enable transport of the at least one magnetic and/or electric label through the first channel. It is an advantage of such embodiments that the transport of magnetic and/or electric particles or magnetisable particles is against the bulk fluid actuation into the second receptacle. The latter may further prevent transport of unwanted components such as e.g. non-reacted reagent to the detection surface in the first receptacle. The detection system may comprise at least a first channel for connecting the at least a first receptacle and the at least a second receptacle.

The detection system may comprise at least a first channel for connecting the at least a first receptacle and the at least a second receptacle, the first channel being adapted for enabling said fluid flow from the at least a first receptacle to the at least a second receptacle by capillary action. It is an advantage of such embodiments that no or little external force means are needed for enabling the predetermined fluid flow.

The at least a first receptacle and/or the at least a second receptacle may comprise a mixing means. It is an advantage of such embodiments that the rate of the assay reaction can be increased through localised mixing.

The at least a first receptacle and/or the at least a second receptacle may be in contact with fluid flow rate modifying moieties. It is an advantage that the flow within the receptacles can be individually controlled. The at least a first receptacle and/or the at least a second receptacle may be directly connected with the fluid flow rate modifying moieties through a connecting channel. The flow rate modifying moieties may be absorbent materials with a predetermined fluid absorptivity.

The at least a second receptacle may comprise a plurality of different reagents for detecting multiple analytes.

The at least a first receptacle may comprise a detection surface for the enabling of detection of a magnetic and/or electric label assisted detection signal, the detection surface having different locations for detection of different targets. It is an advantage of such embodiments that multiplexing can be performed, resulting in efficient and quick analysis of samples. The detection surface of the at least a first receptacle may comprise different designated regions for detecting designated targets. The at least a second receptacle may comprise a set of second receptacles connected to the at least a first receptacle, each receptacle comprising reagents specific for each target to be studied in a multiplex assay.

The at least one magnetic and/or electric label may comprise a plurality of different magnetic and/or electric labels wherein the magnetic and/or electric field generator is adapted for selectively enabling transport for the different magnetic and/or electric labels. The different magnetic and/or electric labels preferably may have at least one unique magnetic and/or electric characteristic that can be selected. It is an advantage of such embodiments that selective transport of labels for multiplexing can be easily performed.

The detection system may comprise a fluid detector in the at least a first receptacle and/or the at least a second receptacle. It is an advantage that the incubation time of the target with the assay reagents can be determined and controlled.

The detection system may comprise a further receptacle for comprising secondary magnetic and/or electric labels and a further magnetic and/or electric field generator for enabling transport of the additional magnetic and/or electric labels from the additional receptacle to the at least a first receptacle. It is an advantage of such embodiments that the detection system allows additionally signal amplification through the addition of a secondary magnetic and/or electric label.

The at least a first receptacle may be adapted for allowing interaction between the sample and assay reagent. The detection system may be adapted for transporting magnetic and/or electric labels from the at least a second receptacle to the at least a first receptacle and for allowing interaction in the at least a first receptacle between the magnetic and/or electric labels and parts of the reacted sample and assay reagent. It is an advantage of the present invention that a good separation between the reagent and the magnetic and/or electric labels can be obtained until the assay reaction has progressed for the desired time.

The at least a second receptacle may be adapted for allowing interaction between the sample, assay reagent and the magnetic and/or electric labels. The detection system may be adapted for transporting magnetic and/or electric labels connected to target components of the sample after interaction between the sample, assay reagent and the magnetic and/or electric labels from the at least a second receptacle to the at least a first receptacle. It is an advantage of the present invention that unreacted reagents can not interfere with the label detection in the at least a first receptacle.

The detection system further may comprise any of a magnetic and/or electric or optical detector for detecting the at least one magnetic and/or electric label. The at least one magnetic and/or electric label preferably may be bound at the detection surface prior to detection. The detection system further may comprise an analysis means for determining the amount of the at least one target molecule. The at least one magnetic and/or electric label may be attached to a magnetic and/or electric particle or magnetisable particle. The detection surface may comprise capture probes for binding the at least one label. It is an advantage of the present detection system that the at least one target molecule is indicative of the presence or absence of an analyte in a sample. The at least one target molecule may be identical to said analyte in said sample. It is an advantage of the present detection system that the labels can be rapidly transported.

The present invention also relates to a method for detecting at least one target molecule, the method comprising the steps of allowing interaction between the sample and at least one magnetic and/or electric label to thereby obtain at least one magnetically and/or electrically labelled target molecule, magnetically or electrically transporting the at least one magnetic and/or electric label to a detection surface, and after said allowing of interaction and transporting the at least one magnetic and/or electric label, detecting at least one magnetic and/or electric label assisted detection signal. The method furthermore may comprise exciting the at least one magnetic and/or electric label, e.g. by irradiating it or by orienting a physical property of the magnetic and/or electric label using an electric and/or magnetic field. The method may comprise providing a fluid flow in a different direction then the magnetically and/or electrically transporting direction, e.g. in a direction substantially opposite to the magnetically and/or electrically transporting direction, i.e. substantially in counter flow.

Transporting the at least one magnetic and/or electric label may comprise transporting the at least one magnetically and/or electrically labelled target molecule obtained by said allowing interaction.

Allowing interaction may comprise allowing interaction between the sample and at least one magnetic and/or electric label after transporting the magnetic and/or electric label to a detection surface.

The method may comprise measuring a detection signal prior to allowing interaction so as to calibrate the detection system. The calibration may be a calibration for specific magnetic and/or electric label-sensitivity.

The method further may comprise capturing the at least one target molecule on the detection surface. The method furthermore may comprise exciting the at least one magnetic and/or electric label, e.g. by irradiating it or by orienting a physical property of the magnetic and/or electric label using an electric and/or magnetic field.

The method further may comprise separating bound and unbound magnetic and/or electric labels before detecting the magnetic and/or electric label assisted detection signal. The at least one magnetic and/or electric label may be attached to a magnetic and/or electric particle or magnetisable particles.

The present invention also relates to a sensor component prepared for use with a detection system for detecting at least one target molecule, the sensor component comprising at least a first receptacle comprising a detection surface, the at least a first receptacle being substantially label-free prior to use, at least a second receptacle comprising, prior to use, at least one magnetic and/or electric label for enabling magnetic and/or electric label assisted detection, the at least one magnetic and/or electric label adapted for interacting with the at least one target molecule, the sensor component adapted for enabling transport of the at least one magnetic and/or electric label from the at least a second receptacle to the at least a first receptacle using a magnetic and/or electric field. The sensor component furthermore may be adapted for enabling a fluid flow from the at least a first receptacle to the at least a second receptacle.

The detection surface may comprise at least a first capture probe. The component further may comprise a predetermined amount of at least one target molecule in a buffer solution. The predetermined amount of at least one target molecule in a buffer solution may serve as a positive control and/or as a standard. The component further may comprise a predetermined amount of at least one magnetic and/or electric label enabled for binding to the at least one target molecule. The component further may comprise a buffer solution free of at least one target molecule, provided as negative control. The component further may comprise magnetic and/or electric particles or magnetisable particles. The sensor component may be a disposable device.

It is an advantage of the present detection system that the labels are separated rapidly after interaction with the target molecules.

It is an advantage of embodiments of the present detection system and/or method that the assay reactions involving a target or target homologue and the detection of the magnetic and/or electric labels by the sensor.

It is an advantage of embodiments of the present detection system and/or method that bulk fluid actuation steps are minimized.

It is an advantage of embodiments of the present detection system and/or method that unreacted reagents are hindered from entering the detection receptacle. The latter may be in methods and systems for the transport of magnetic and/or electric labels from a reaction receptacle to a detection receptacle.

It is an advantage of embodiments of the present detection system and/or method that the at least one target molecule is indicative of the presence or absence of an analyte in a sample. The at least one target molecule may be identical to said analyte in said sample.

Particular and preferred aspects of the invention are set out in the accompanying independent and dependent claims. Features from the dependent claims may be combined with features of the independent claims and with features of other dependent claims as appropriate and not merely as explicitly set out in the claims. The teachings of the present invention permit the design of improved methods and apparatus for detecting chemical, biological and/or biochemical particles.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1A:
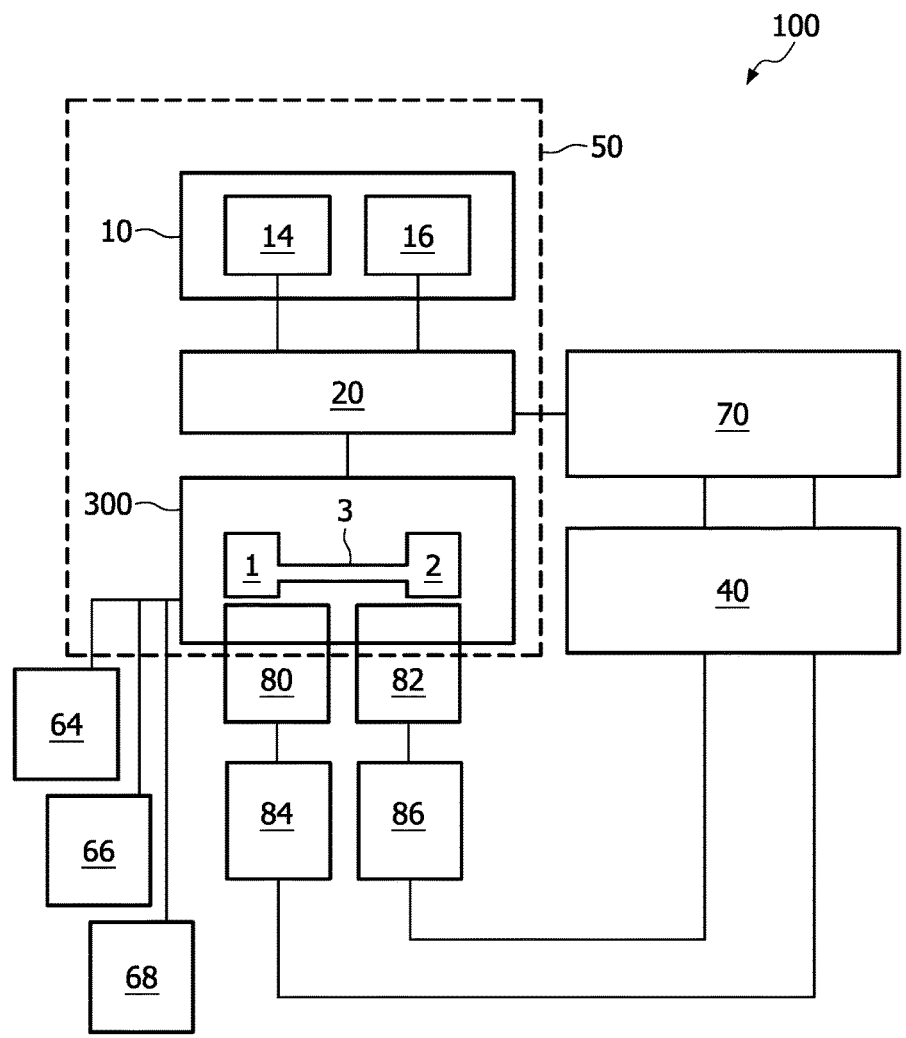
FIG. 1a and FIG. 1b are schematic representations of an exemplary detection system according to a particular embodiment of a first aspect of the present invention (FIG. 1a) and an enlarged view of a sensor component thereof (FIG. 1b).

In the different figures, the same reference signs refer to the same or analogous elements.

DETAILED DESCRIPTION OF THE EMBODIMENTS

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. These definitions should not be construed to have a scope less than understood by a person of ordinary skill in the art. The term "receptacle", as used herein, relates to a space wherein components of the assay or sample may be present, such as e.g. a reaction volume and a detection volume. A receptacle thus is something to receive or contain matter in. A receptacle may be closed or open. It may e.g. refer to a chamber. It does not necessarily imply that walls need to be present, although this may be the case. It also may refer to a well, such as e.g. a well in a microtiter plate format or any other suitable container.

The term "sample", as used herein, relates to a composition which may comprise at least one analyte of interest. The sample is preferably a fluid, also referred to as "sample fluid", e.g. an aqueous composition.

The term "analyte", as used herein, refers to a substance whose presence, absence, or concentration is to be determined according to the present invention. Typical analytes may include, but are not limited to small organic molecules, metabolites such as glucose or ethanol, proteins, peptides, nucleic acid segments, molecules such as small molecule pharmaceuticals, antibiotics or drugs, molecules with a regulatory effect in enzymatic processes such as promoters, activators, inhibitors, or cofactors, viruses, bacteria, cells, cell components, cell membranes, spores, DNA, RNA, micro-organisms and fragments and products thereof, or any substance for which attachment sites, binding members or receptors (such as antibodies) can be developed. Presence, absence or concentration of the analyte may be determined directly by assessing the presence, absence or concentration of the analyte itself, or may alternatively be determined indirectly by assessing the presence, absence or concentration of a target or target molecule.

The term "target" or "target molecule", as used herein, refers to a substance whose presence, absence, or concentration is actually determined according to the present invention. The term "target molecule" should be construed broadly and can be, for example, an individual molecule, can be a cluster of molecules, can be a complex of molecules, can be a molecule embedded in other material such as a substrate, etc. The target and analyte may be identical, or the target may be indicative of the presence or absence of the analyte. In particular, targets such as proteins or DNA may be a distinctive component or product of analytes such as viruses, bacteria, or other organisms, and therefore indicative of their presence. Where detection involves an enzymatic assay, the target may be a product of an enzymatic conversion of a substrate by an enzyme, and may therefore be indicative of the amount of substrate or the activity of the enzyme. Target molecules may also be polymers, metal ions, and low molecular weight organic species such as toxins, illicit drugs, and explosives, the invention clearly not limited thereto. During the detection assay, the target may become labelled to emanate a detectable signal. The target may also be retained or become immobilised on the detection surface as part of a biologically-active coating.

The term "label", as used herein, refers to a molecule or material capable of generating a detectable signal or capable of binding to another molecule or forming a complex which generates a detectable signal. Suitable labels for use in the different detection systems and methods of the present invention are numerous and extensively described in the art. These may be optical labels, radioactive labels, magnetic and/or electric labels, etc. Labels can be direct labels, which can directly be detected by a sensor. Alternatively, labels can be indirect labels, which become detectable after a subsequent development process. Typically, the label used in the methods of the present invention is a target-specific label, i.e. capable of binding specifically to the target. Nevertheless it is also envisaged that where the target is present in a purified form, it is sufficient that the label binds to the target. Magnetic labels envisaged within the context of the present invention include, but are not limited to, metal or magnetic beads or nanoparticles. The magnetic label may include any suitable form of one or more magnetic particles or magnetisable particles e.g. magnetic, diamagnetic, paramagnetic, superparamagnetic, ferromagnetic that is any form of magnetism which generates a magnetic moment in a magnetic field, either permanently or temporarily. Examples of suitable magnetic label material are e.g. $Fe_3O_4$ beads. The size of the magnetic label is not critical in most embodiments but preferably may be of a small size, e.g. having a longest diameter in the range 5 nm to 5000 nm, more preferred 50 nm to 1000 nm. Detection of a magnetic label is generally done by application of an electric, or magnetic, or electromagnetic field and using a magnetic or non-magnetic, e.g. optical or acoustic sensor. Acoustic and/or sonic detection of labels may also be used. Unless specified the magnetic label refers to the molecule or material as such, not covalently linked to a probe. The magnetic label may be attached to a probe, a capture probe, a substrate, a target, or an analyte, preferably through covalent binding but other types of binding such as hydrogen binding are also possible. Depending on the type of assay being performed, labelled target molecules either bind to immobilized capture probes (sandwich assay), or compete with target analogues to bind to capture probes (competitive assay). After removal of excess (unbound) magnetic label, the amount of bound magnetic label is measured. Thus, binding assays may typically involve adherence of magnetically labelled binding molecules to a solid substrate in numbers that reflect the concentration or presence of the target molecule. Alternatively, magnetically labelled binding molecules such as magnetically labelled target analogues may be bound to the detection surface and the displacement of or inhibition of magnetically labelled target analogues by target molecules may result in a decrease of magnetic labels near the detection surface. A large number of variations on binding assay methodologies have been described and are all within the scope of the present invention. The various types of binding and releasing assays may use magnetic labels that comprise optical properties such as e.g. fluorescent, chromogenic, scattering, absorbing, refracting, reflecting, SERRS-active or (bio)chemiluminescent labels, molecular beacons, radioactive labels, or enzymatic labels. Optically active labels typically may emit light detectable by a detector, e.g. in the visual, infrared or ultraviolet wavelength region. Nevertheless, the invention is not limited thereto and optical labels, in the present application, may refer to labels emitting in any suitable and detectable wavelength region of the electromagnetic spectrum. Alternative to magnetic labels or in addition thereto, electric labels could be used. Electric labels refer to labels having a detectable charge property, dielectric property, charge-transfer property, or a charge-generating property (e.g. via a redox-active moiety). Electric labels further may comprise characteristics and features equal to or similar to the labels described above.

The term "probe", as used herein, refers to a binding molecule that specifically binds a target molecule. Probes envisaged within the context of the present invention include biologically-active moieties such as whole antibodies, antibody fragments such as Fab' fragments, single chain Fv, single variable domains, VHH, heavy chain antibodies, peptides, epitopes, membrane receptors or any type of receptor or a portion thereof, substrate-trapping enzyme mutants, whole antigenic molecules (haptens) or antigenic fragments, oligopeptides, oligonucleotides, mimitopes, nucleic acids and/or mixtures thereof, capable of selectively binding to a potential target molecule. Antibodies can be raised to non-proteinaceous compounds as well as to proteins or peptides. Probes are typically members of immunoreactive or affinity reactive members of binding-pairs. The nature of the probe will be determined by the nature of the target to be detected. Most commonly, the probe is developed based on a specific interaction with the target such as, but not limited to, antigen-antibody binding, complementary nucleotide sequences, carbohydrate-lectin, complementary peptide sequences, ligand-receptor, coenzyme-enzyme, enzyme inhibitors-enzyme, etc. Probes also include "capture probes" for immobilizing targets and/or labeled targets on the detection surface via recognition or binding events. Probes and capture probes may be labeled. Where a target molecule is immobilized through binding to a capture probe the resulting complex is referred to as a "target-capture complex". Where the label used in the devices and methods of the present invention is a target-specific label, this can be ensured by using a target-specific probe bound to a label. Where the target is a protein, the target-specific probe can be an anti-target antibody. Alternatively, where the target is a nucleotide sequence, the target-specific probe can be a complementary oligonucleotide sequence.

The term "target analogue", as used herein, refers to a substance that can associate with a probe or capture probe less optimally than the target. The target analogue is used in competitive assays where the target is determined based on competition with the target analogue, e.g. in the competitive binding to a probe or capture probe. In particular, the target analogue binds to a probe or capture probe with a reduced binding strength compared to the binding of the target to probe or capture probe.

Figure 1B:
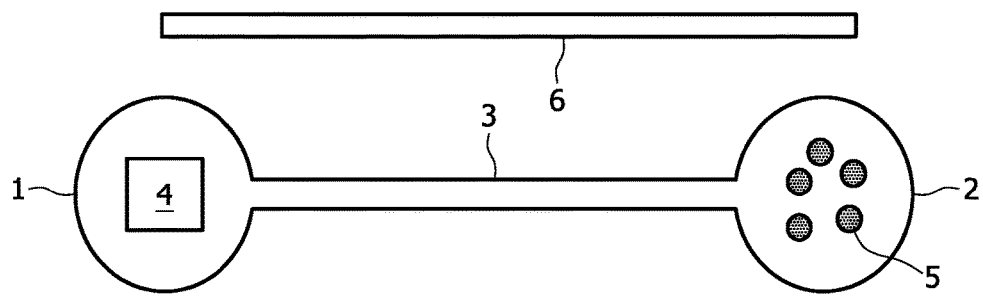

According to a first aspect, the present invention provides a detection system 100 for detecting and/or quantifying at least one target molecule, and thus analyte, in a sample. Such a detection system may for example be a detection system for detecting chemical, biological or bio-chemical particles, the invention not being limited thereto. The detection system may indicate presence of a target molecule or derived therefrom analyte in the sample. The detection system comprises at least a first receptacle and at least a second receptacle. These preferably are interconnected by means of a first channel. The at least first receptacle comprises a detection surface whereon detection of the target molecule may be performed. The first receptacle also is substantially magnetic label-free prior to use, i.e. substantially no magnetic label is present prior to use of the detection system. The at least second receptacle comprises at least one magnetic label for enabling magnetic-label assisted detection. The latter may be present, prior to use, in the second receptacle or it may be added to the second receptacle from a magnetic label supply e.g. when initiating the use of the detection system, or may be present in the channel and introduced to the second receptacle by means of a transport force. The at least one magnetic label is adapted for interacting with the target molecules, e.g. by binding to the target molecule. The detection system also comprises a magnetic field generator for enabling transport of the at least one magnetic label from the at least a second receptacle to the at least a first receptacle, e.g. through the at least a first channel, thereby enabling detection of a magnetic label assisted detection signal. The magnetic field generator may generate a magnetic field gradient for moving magnetic or magnetisable particles. It is to be noted that where in the present description reference is made to magnetic labels, magnetic field, magnetic field generator etc. a similar method and device related to electric labels, electric field, electric field generator etc. also is envisaged by and within the scope of the embodiments and aspects of the present invention. Standard and optional components of an exemplary detection system 100 according to the present invention are shown in FIG. 1a and FIG. 1b and will be further described in more detail below, the detection system not being limited thereto.

The detection system 100 comprises at least a first receptacle 1 and at least a second receptacle 2. The at least a first receptacle 1 and the at least as second receptacle 2 preferably are connected with each other, for example by at least a first channel 3. The at least a first receptacle 1 comprises a detection surface 4. At least part of the detection surface 4 may be adapted for label-assisted detection. The detection surface 4 may e.g. be the surface of a sensor chip, either being disposable or not. One way of being adapted for label-assisted detection is using capture probes retained and/or attached and/or immobilised on the detection surface 4. Capture probes may refer to a layer of biologically-active or biochemically active moieties that are capable of binding, or that are reactive with, a target or a labelled probe. They may be retained or immobilized on the surface by any method known in the art. For instance, capture probes may be attached to the detection surface 4 in a site-specific manner meaning that specific sites on these capture probes are involved in the coupling to the carrier chip. The detection surface 4 may be a porous surface in order to enhance the surface-over-volume ratio. Prior to use, the at least a first receptacle 1 does not comprise labels, or in other words it is substantially free of magnetic labels. The latter remains the case till after interaction between reagents and the sample fluid.

On the other hand, the at least a second receptacle 2 comprises at least one magnetic label 5 for magnetic label assisted detection after interaction with the target molecule. In a preferred embodiment the magnetic labels may be provided in a dry and a rapidly dissolvable form. This allows the biosensor to be delivered in cartridge or disposable form. The at least one magnetic label 5 is provided for interaction with the target molecule which may typically be through a binding assay. Through the use of magnetically labelled binding molecules, the binding or recognition events may typically generate a detectable signal and indicate the presence or absence or activity of a target molecule. Binding and releasing assays as envisaged in the present invention include immunoassays, DNA hybridization assays, and receptor-based assays that are widely used in the medical community as diagnostic tests for a wide range of target molecules. Possible assays also include sandwich assays, anti-complex assays, and blocking agent assays, see for example The Immunoassay Handbook published by Elsevier Science and edited by David Wild. For example, in a sandwich assay target molecules interact with capture probes attached to the detection surface 4 and the at least one magnetic label 5 bind to the target molecules so that detection of the magnetic labels near the sensor chip is enabled.

In use, the assay reaction may either occur on or near the magnetic label 5 in the second receptacle 2, i.e. away from the detection surface 4. Alternatively, the assay reaction may occur near or on the detection surface 4, i.e. in the first receptacle 1, without the at least one magnetic label 5 being in the neighbourhood. In other words, the at least a first receptacle 1 as well as the at least a second receptacle 2 may act as reaction receptacle. In the reaction receptacle both sample fluid and reagent are provided to interact. The at least a first receptacle 1 and/or the at least a second receptacle 2 therefor may comprise reagents of biological, chemical or biochemical nature for reacting with the target thus assisting in allowing detection of the presence of the analyte in the sample. Suitable reagents for use in the different detection systems and methods of the present invention include a variety of active components selected to assist in determining the presence and/or concentration of various analytes. The selection of appropriate reagents is well within the skill in the art. As is well known in the art, there are numerous chemistries available for use with each of various targets. In a preferred embodiment the reagents may be provided in a dry and a rapidly dissolvable form, e.g. as a dissolvable reagent layer.

The above described elements may be grouped in a sensor component 300, sometimes referred to as a sensor chip, which may be a re-usable part or a disposable part of the detection system.

The detection system 100 furthermore comprises a magnetic field generator 6 enabling the transport of the at least one magnetic label 5 from the second receptacle 2 to the first receptacle 1. Depending on where the assay has taken place, either the at least one magnetic label 5 as such or the at least one magnetic label 5 coupled to the at least one target molecule, also referred to as magnetically labelled target molecule, may be transported. Transport of the at least one magnetic label 5 thus preferably is performed by applying a magnetic field having an orientation adapted for enabling transportation of the magnetic label 5, e.g. by providing a suitably directed magnetic field gradient. Preferably the magnetic field generator may be controlled, i.e. turned ON or OFF or even set to predetermined magnetic field characteristics, such that transport of the at least one magnetic label 5 may be performed when appropriate. The applied magnetic field may be e.g. applied using any of a permanent magnet, an electromagnet wherein for example a magnetic core is present, a coil or a number of coils wherein for example the current may be controlled, etc. The permanent magnet may be mechanically moved in order to control the magnetic field generated. Such magnetic-field generator 6 may be part of the sensor component 300 comprising the fluid receptacles, may be part of a disposable cartridge 50 comprising such a sensor component 300 or may be integrated in another part of the detection system 100, such as e.g. in a reusable reader for a disposable cartridge. For example, a magnetic pen may be used to which the at least one magnetic label 5 is attracted and which transports the at least one magnetic label 5, e.g. through the channel 3. Magnetic field generators 6, such as e.g. current wires, may have limited field extent and thus several magnetic field generators 6, e.g. current wires, can be placed in receptacle 1 and/or receptacle 2 and/or if present in a connection channel 3 between these receptacles 1, 2. The magnetic field may be actuated in a sequence such that the at least one magnetic label is propelled towards receptacle 1 and finally towards the detection surface 4. E.g. in the case of current wires, the current wires may be actuated in sequence to transport the magnetic labels 5. The magnetic field can be DC or AC. AC can sometimes be preferable to prevent the irreversible clustering of magnetic labels.

In order to detect the magnetic label-assisted signal, the detection system 100 may comprise at least one detector 80 for detecting magnetic labels on or near the detection surface 4. The detector 80 may be incorporated in sensor component 300, thus typically resulting in a lab-on-chip biosensor, or it may be incorporated in the detection system 100 but outside a sensor component 300 comprising the detection surface 4. Typically in a lab-on-chip set-up, the active elements of the detector 80 are positioned in a chip carrier of a sensor chip comprising the detection surface 4, whereas the detected signal typically may be converted and transferred to a read-out device external to the sensor component 300. The at least one detector 80 may be a magnetic detector such as e.g. a Hall detector or a magneto-resistive detector such as e.g. an AMR (anisotropic magneto-resistance) detector, a GMR (giant magneto-resistance) detector, or a TMR (tunneling magneto-resistance) detector. Magnetic sensor elements based on other principles such as SQUIDS are also possible for application in the claimed detection system 100. The detector 80 may also be based on other principles for detecting magnetic particles or magnetisable particles and may therefore also be a force amplified biological sensor (FABS), a cantilever-beam force transducer, a microbalance, an impedance meter, or an AFM wherein forces from/on magnetic or magentisable particles are detected. The detection of magnetic beads can also occur based on optical principles such as absorption, scattering, fluorescence, etc. Alternatively or in addition thereto, the detection of magnetic beads can also occur based on acoustic and/or sonic principles. As such, detector 80 may be an optical detector means (e.g. absorption, scattering, fluorescence, etc), an electrical detector means (e.g. impedance), an acoustic detector, a means of mass detection, etc. This can be done by the measurement of a direct property of the magnetic label 5 or it can result from a measurement of a property stemming from the modification of the magnetic label 5, for example via the attachment a second label such as an enzymatic label e.g. peroxidase, phosphatase, or oxidase, an electrochemical label or a fluorescence label e.g. a core shell magnetic label in which the core contains the magnetic species and the shell has a fluorescent dye or vice versa. In other words, also label multiplexing may be performed, whereby different labels types of labels are used and detected in combination with some use of the magnetic label in the detection process. E.g. labels with different optical properties (fluorescence, shape, color, etc.) or magnetic properties (relaxation time) or electrical properties (e.g. redox potential) can be used as secondary label.

The detector 80 may be connected to detector driving circuitry 84 for driving, e.g. controlling, the detector 80. The detector 80 may be adapted, e.g. in position or by providing additional focusing components, for detecting magnetic labels or a detectable signal thereof at the detection surface 4.

The detection system 100 furthermore may comprise an excitation means 82 adapted for exciting the at least one magnetic label 5 used. Depending on which magnetic labels used, the excitation means 82 may e.g. be an optical excitation means or a mechanical excitation means or a magnetic excitation means, including AC and DC magnetic excitation means. The excitation means 82 may be controlled by an excitation means driving circuitry 86. A magnetic excitation means may e.g. be an electromagnetic unit for generating an electromagnetic field for applying an electric or magnetic field to a sample containing at least one magnetic label 5 in order to orientate the at least one magnetic label 5 such as an electromagnet, an air-cored wire coil, a straight wire, a conductive micro-fabricated trace, a permanent magnet. a coil. The magnetic excitation means 82 may e.g. be a second magnetic field generator that creates a magnetic field for magnetizing and orientating the at least one magnetic label 5. Alternatively, the magnetic field generator 6 may also be used for exciting the magnetic labels, besides for the transporting of the at least one magnetic label 5. The magnetic excitation means also may be positioned outside the detection system 100. It may be an external magnetic excitation means 82 or it may be integrated in a re-usable or disposable component of the detection system 100, e.g. a cartridge 50 comprising a sensor component 300. The detection system 100 may further comprise an analysis circuitry 40 adapted for processing detection signals or signals corresponding therewith. It typically may be adapted to carry out predetermined algorithms for processing the obtained detector results. The analysis circuitry 40 may be adapted for determining a concentration or distribution of an analyte in a sample and/or for processing the obtained detection results e.g. to determine enzyme activity.

Further optional and/or preferred components of the detection system 100 are known by the person skilled in the art and may include a sample containing means 10 for containing the sample prior to performing the assay and a sample providing means 20, optionally controlled using a fluid flow controlling means 70. The sample providing means 20 may include gravimetric feeds of the fluid and may also include an arrangement of pipes/conduits and valves, e.g. selectable and controllable valves, to allow the provision of the fluids from a means 11 for containing sample fluid and a means 12 for containing a control sample to the sensor chip 4. Alternatively, the fluids may be actively or passively pumped from the means 11, 12 to the sensor chip 4. The detection system 100 also may comprise a vent for allowing gas to escape, in order to have an appropriate filling of the receptacle. The sample containing means 10 typically may comprise a sample container 14 for holding the sample to be studied and optionally also may comprise a reference container for holding a reference or control sample. Other optional components may include an assay facilitating means 64 to assist dissolution of the dissolvable reagent layer, assist diffusion of dissolved components on or near the detection surface 4, and to facilitate the assay reactions between the various components of the reaction such as magnetic labels, target molecules, capture probes, etc, a temperature control means 66 to control the temperature for ensuring appropriate temperatures in the receptacles 1, 2, a cleaning means 68, for cleaning the detection system or part thereof, such as e.g. the receptacles 1, 2 and, if present, the channel 3, etc. Often a detection surface 4 may contain an array of different detection surfaces 4, for so-called sensor multiplexing. Alternatively, different receptacles may each contain a different detection surface 4 for detecting different components or properties. Different detection surfaces 4 can be used to detect different biological molecules, they can be used as positive or negative control, or can be used for calibration purposes. Further embodiments and examples according to the first aspect are provided below, the invention not being limited thereto.

Figure 2:
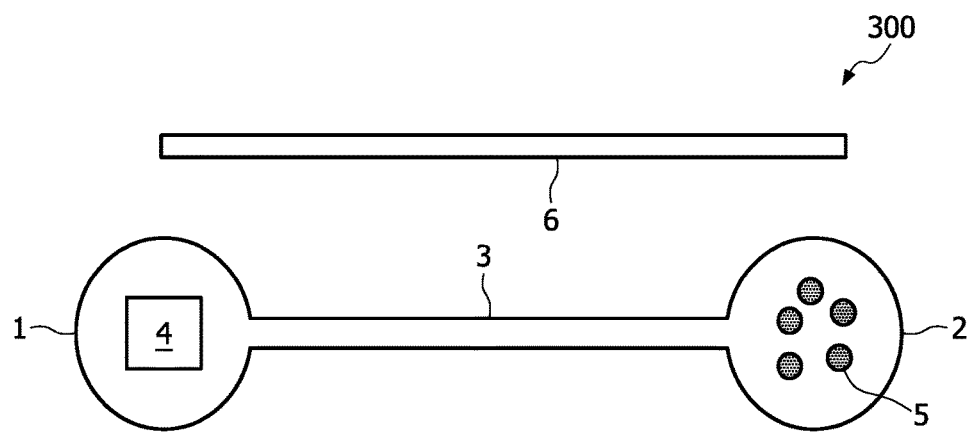
FIG. 2 is a schematic representation of a detection device component according to a particular embodiment of the first aspect of the present invention prior to transportation of magnetic and/or electric labels.
Figure 3:
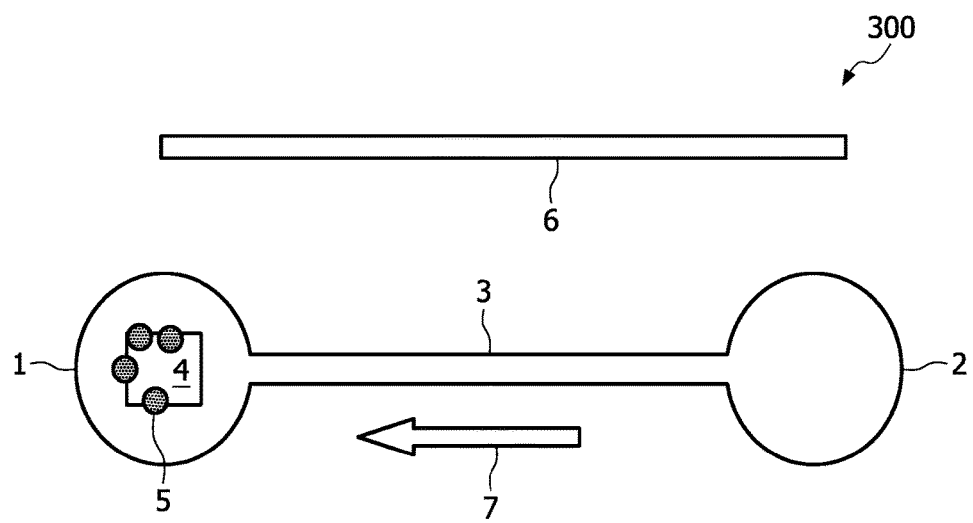
FIG. 3 is a schematic representation of a detection device component according to a particular embodiment of the first aspect of the present invention, after magnetic and/or electric label transportation.

The principles of the first and second particular embodiment are further illustrated by way of FIG. 2 and FIG. 3, FIG. 2 thereby illustrating the situation prior to transport of the at least one magnetic label 5 and FIG. 3 illustrating the situation after transport of the at least one magnetic label 5.

In a first particular embodiment, a detection system 100 as described above for the first aspect is provided, comprising the same features and advantages, wherein the assay reaction occurs on the at least one magnetic label 5. The detection system 100 therefore is such that the second receptacle 2 is provided with at least one magnetic label 5 or with an inlet for at least one magnetic label 5. The assay reaction begins once the second receptacle 2 is filled with the sample fluid and the reagents and at least one magnetic label 5 is released or present within the second receptacle 2. In the case where, for later detection, magnetic label binding to the detection surface 4 is required, preferably at least one of the reagents is designed so that it can bind to both the at least one magnetic label 5 and, later after transportation, to the detection surface 4. Such binding can be done directly to the magnetic label 5 and/or to the detection surface 4 or through molecules that are attached thereto such as capture probes. After a certain time of interaction in the second receptacle 2, the at least one magnetic label 5, having reacted with reagents and with sample fluid, are transported using the magnetic field generator 6 from the second receptacle 2 to the first receptacle 1, e.g. through an interconnection channel 3. The transport of the magnetic particles or magnetisable particles is indicated by arrow 7 in FIG. 3. The at least one magnetic label 5 having reacted with the reagents in the presence of the target or target homologue can now be detected at the detection surface 4 in the first receptacle 1. If binding to the detection surface 4 is required, this binding will occur after transportation from the second receptacle 2 to the first receptacle 1. Because the reagents are non-magnetic, they will remain in receptacle 2 if they are not attached to the magnetic label 5, and thus cannot interfere with the magnetic label detection in the first receptacle 1. In other words, unreacted reagents remain in the second receptacle 2 and do not interfere with the magnetic label-assisted detection in the first receptacle 1. The amount of magnetic label 5 detected at the detection surface 4 is related to the concentration of the target or target homologue. The advantage of this solution for the above assay is that unreacted reagents in the second receptacle 2 do not interfere with the magnetic label-based detection or with the magnetic label binding to the detection surface 4 in the first receptacle 1. Because the diffusion of reagents not bound to the magnetic label is slow, very few reagents will be able to leave the second receptacle 2 and enter the first receptacle 1. The diffusion characteristic of reagents typically may be expressed by their diffusion length, given by the square root of the product of diffusion coefficient times the diffusion time. It can e.g. take hours for a protein to diffuse over a distance of a millimeter in a static fluid. The inter-receptacle diffusion flux can even be further reduced by increasing the length of an interconnection channel 3 between the first receptacle 1 and the second receptacle 2 and/or by decreasing the cross-section of the interconnection channel 3. In contrast, the movement of the magnetic label 5 will be fast due to their active transport with a magnetic force. As mentioned above, the present invention also relates to the use of electric labels transported through electric forces, e.g. through electrophoresis and dielectrophoresis.

In a second particular embodiment, a detection system as described above for the first aspect is provided, comprising the same features and advantages, wherein the assay reaction occurs on the detection surface 4 in the first receptacle 1. The first receptacle 1 thus is adapted for being filled with sample fluid and for being provided with reagents. The assay reaction begins once receptacle 1 is filled with the sample and the reagents are released into first receptacle 1. After a certain reaction time, the at least one magnetic label 5, provided or present in the second receptacle 2, are transported using the magnetic field generator 6, i.e. pulled with a magnetic force, from the second receptacle 2 to the first receptacle 1, e.g. through interconnection channel 3. The detection surface 4 having reacted with the reagents in the presence of the target or target homologue can now bind to the at least one magnetic label 5. The advantage of this solution is that unreacted reagents in the first receptacle 1 do not prematurely bind with the at least one magnetic label 5 in the second receptacle 2, thus reducing the number of non-usable magnetic label bindings. For example, binding between reagent and the at least one magnetic label, prior to availability of the sample fluid is avoided. Because the diffusion of reagents is slow, very few will be able to leave the first receptacle 1 and enter the second receptacle 2 and bind to the magnetic labels. Furthermore, very few magnetic labels 5 will be able to leave the second receptacle 2 and enter the first receptacle 1 prior to their active transportation, i.e. until the assay reaction has progressed for the desired time and the active transportation is initiated.

Figure 4:
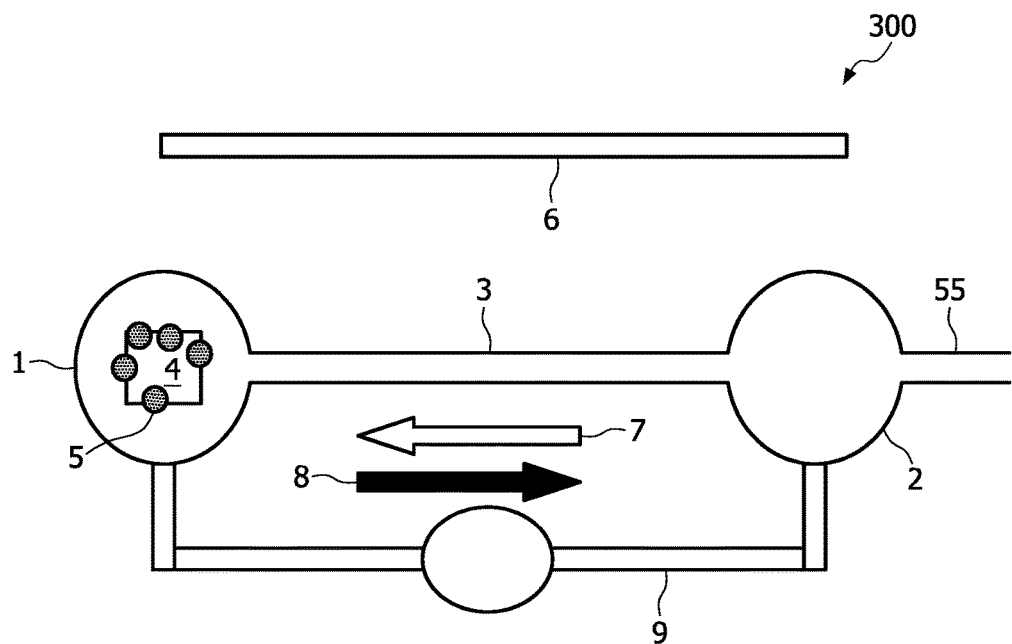
FIG. 4 is a schematic representation of a detection device component comprising a fluid control means according to a particular embodiment of the first aspect of the present invention.
Figure 5:
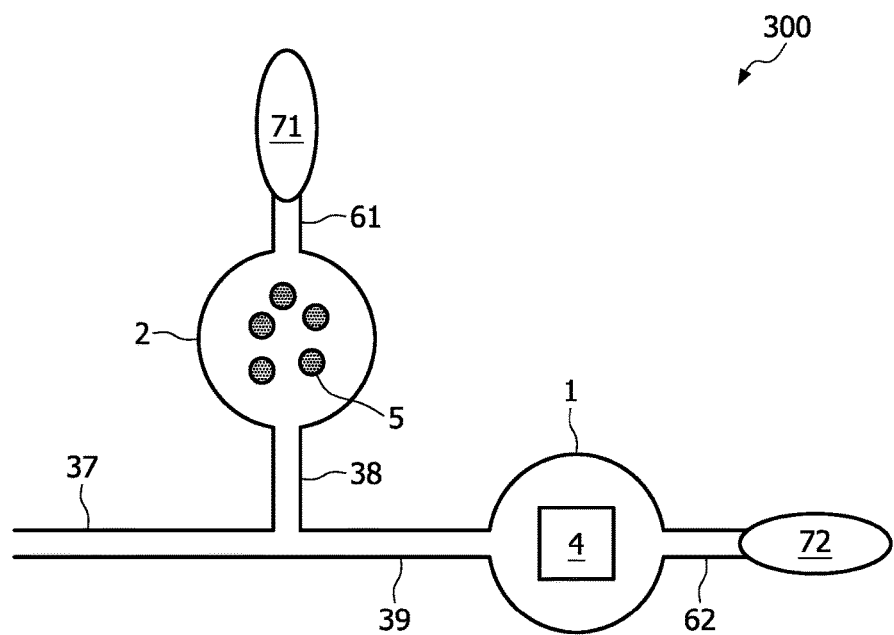
FIG. 5 is a schematic representation of a detection device component comprising fluid flow controlling moieties according to a particular embodiment of the first aspect of the present invention.

In a third particular embodiment, a detection system as described above, e.g. in the first embodiment although not limited thereto, is provided comprising the same features and advantages, wherein the diffusion of unreacted reagents from the second receptacle 2 to the first receptacle 1 can be further suppressed by a valve in the channel or by a flow in the direction from the first receptacle 1 to the second receptacle 2. Such a flow may be generated by a fluid flow control device 9 in any suitable way, e.g. using for example the capillary action from filling the receptacles or it may e.g. be obtained by the application of an over-pressure on the first receptacle 1 and/or an under-pressure applied to the second receptacle 2. The flow control device may be placed outside the channel or inside the channel. An example of a fluid flow device inside the channel is an array of micromechanical flaps which can set the fluid into motion. The flow control device 9 may be a pump. The latter is illustrated in FIG. 4 using arrow 8. The flow within and/or between the first and second receptacle 1, 2 can optionally be controlled individually, i.e. per receptacle. In particular examples of this embodiment, the flow control device 9 may be substantiated by connecting the first receptacle and/or second receptacle to fluid flow rate modifying moieties 71, 72 through channels 61, 62. The latter is illustrated in FIG. 5. These fluid flow modifying moieties 71, 72 can be for example absorbent material with various fluid absorptivity. It is advantageous in the case where the assay reaction first occurs on the surface of sensor chip 4 to have a flow, e.g. a weak flow, out of the first receptacle 1 towards moiety 72 to prevent or reduce unreacted reagents entering the second receptacle 2 and to remove or reduce the amount of unreacted reagents in the first receptacle 1 before the magnetic labels 5 are transported from the second receptacle 2 to the first receptacle 1. Valves at the openings of the first receptacle 1 and the second receptacle 2 towards 71, 72 can be included to control individually the time at which flow out of the first and/or second receptacle is introduced. For example, it is desirable to allow the sample to incubate with the reagents in the first receptacle 1 for some time before flow toward moiety 72 is initiated. The lengths and diameters of channels 61, 62 can be made small to prevent loss of reagent material. In the case that the reagents are already on the magnetic labels 5 and the addition of the analyte releases the moiety that allows the magnetic labels 5 to be detected in solution or detected by binding to the detection surface 4, e.g. in the case of the inhibition, competitive, displacement, or enzymatic assays, a flow of the sample from the first receptacle 1 to the second receptacle 2 and then out of the second receptacle 2 through channel 55, as illustrated in FIG. 4, is advantageous. This way the released moiety is washed away and the chance of it entering receptacle 1 and binding to the surface of sensor chip 4 is significantly reduced. To avoid that the magnetic labels 5 are also washed away, a magnetic forced can be used to keep the magnetic labels 5 in the second receptacle 2. After the desired reaction time, the magnetic labels 5 can then be transported to the first receptacle 1. In other words, fluid flow control means 9 may be provided adapted to control the fluid flow as to control the interaction and/or separation between magnetic labels 5 and reagents.

In a fourth particular embodiment, a detection system 100 as described above is provided, for example but not limited to any of the above described particular embodiments, wherein the rate of assay reaction in the first receptacle 1 and/or the second receptacle 2 is adapted, e.g. increased, through localized mixing. The detection system 100 therefore may comprise a mixing means in the first receptacle and/or the second receptacle. Such a mixing means may be any suitable mixing means, such as for example a magnetically mixing means which preferably comprises a magnetic stirring means and a magnetic actuator, a mechanically stirring means or may be for example a thermally stirring means.

Figure 6:
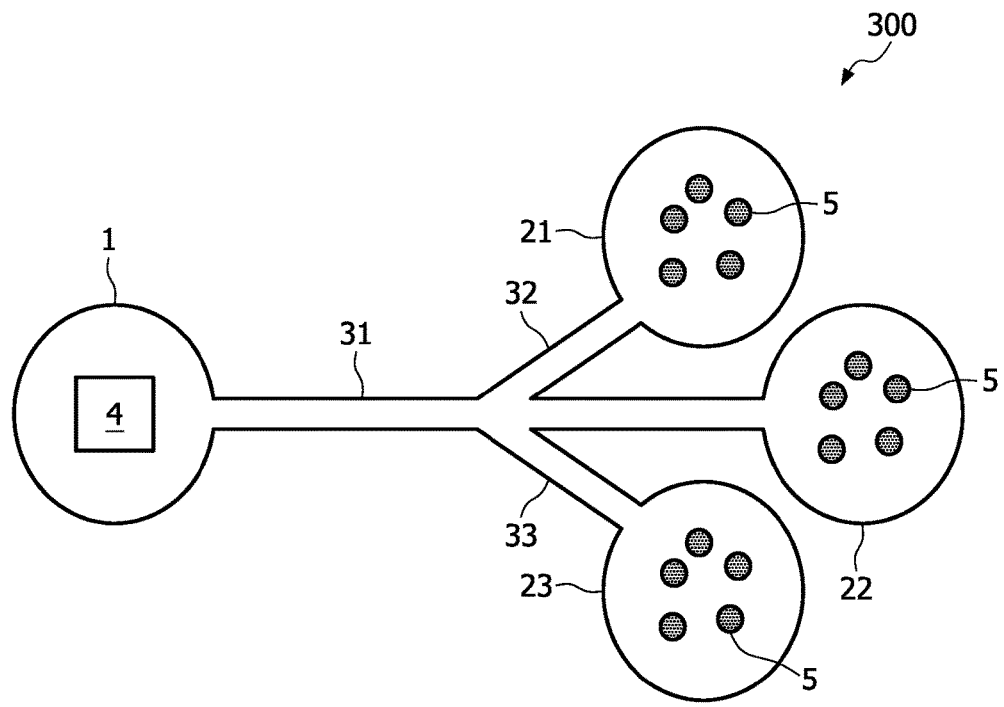
FIG. 6 is a schematic representation of a detection device component comprising multiple reaction receptacles according to a particular embodiment of the first aspect of the present invention.
Figure 7:
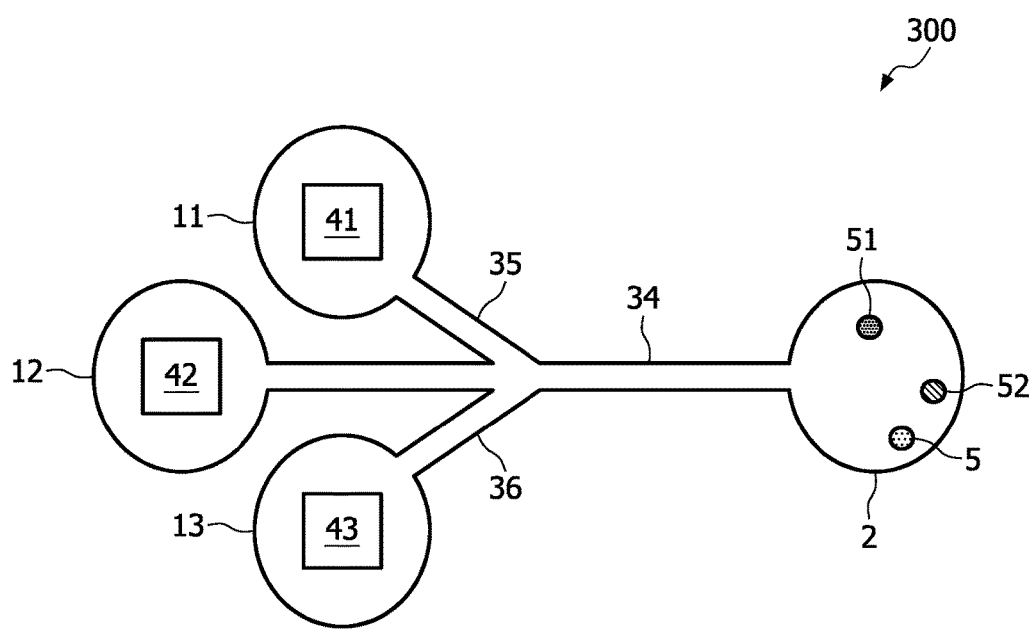
FIG. 7 is a schematic representation of a detection device component comprising multiple detection receptacles according to a particular embodiment of the first aspect of the present invention.

In a fifth particular embodiment, a detection system 100 as described above, for example but not limited to any of the previous embodiments, is provided, comprising the same features and advantages, wherein the detection system is adapted for detection of multiple analytes. There are several possible configurations of the device, some of them illustrated in FIG. 6 and FIG. 7 by way of illustration. One configuration comprises a first receptacle 1 with a detection surface 4 that is able to bind magnetic labels 5 at several different locations, at least one area for each target, and a second receptacle 2 connected to the first receptacle 1 by an interconnection channel 3. In the case that the reaction occurs in receptacle 1, the reagents are chosen that the target can only bind to specific locations on the detection surface 4. The second receptacle contains the at least one magnetic particle or magnetisable particle 5, which can bind to the reacted detection surface. In the case that the reaction takes place in receptacle 2, the second receptacle 2 contains reagents specific for each target and contains the at least one magnetic particle or magnetisable particle 5 which may be specific for each target, e.g. the magnetic particles contain capture probes specific to the target. The reagents preferably are chosen such that when the magnetic particle or magnetisable particle 5 reacts with the target and the magnetic particle or magnetisable particle 5 preferably has the ability to only bind to a designated part of the detection surface 4. After the reactions with the target have occurred the magnetic labels 5 are transported to the first receptacle 1, using magnetic field generator 6, i.e. with a magnetic force, and are allowed to bind to the corresponding area on the detection surface 4. Another structure consists of a first receptacle 1 containing a detection surface 4 with multiple binding areas and a set of second receptacles 21, 22, 23 connected to the first receptacle 1 by channels 31, 32, 33, as shown in FIG. 6. These channels may merge to form one channel for entering the first receptacle. Each second receptacle 21, 22, 23 contains reagents specific for each target and magnetic labels 5 which may or may not be target-specific. Additionally or alternatively thereto, the detection system may have several first receptacles 11, 12, 13 each containing a detection surface 41, 42, 43 specific for each target to be measured, as shown in FIG. 7. This can be combined with a single second receptacle 2 or multiple second receptacles 21, 22, 23. It is desirable in the case that multiple 11, 12, 13 are used, to have them connected to one single input for the sample so that the sample does not have to be dispensed individually into the receptacles 11, 12, 13.

In a sixth particular embodiment, the detection system 100 of the present invention can be any of the above described detection systems designed to detect multiple analytes as described above, furthermore designed to use magnetic labels 5 with varying magnetic properties for detecting predetermined targets. For each target are magnetic labels 51, 52, 53 chosen with at least one unique magnetic characteristic that can be selected. For example, the frequency dependence of the particle magnetization can be used to attract only magnetic labels to receptacle 1 which are responsive to this frequency. The magnetic field generator 6 then may be adapted for selectively transporting different magnetic labels having different magnetic properties. For example, the magnetic field generator 6 may have a selectable magnetic field frequency. Alternatively or in addition thereto, different magnetic field generators 6 may be provided, each being adapted for generating a magnetic force for transporting magnetic labels having predetermined magnetic characteristics.

Figure 8:
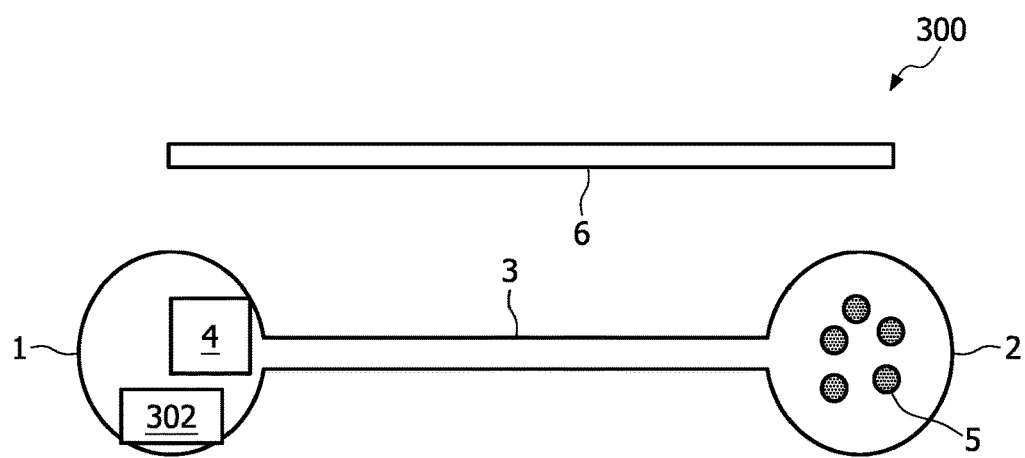
FIG. 8 is a schematic representation of a detection device component comprising a fluid detection means according to a particular embodiment of the first aspect of the present invention.

In a seventh particular embodiment, the detection system 100 of the present invention may include a fluid detector 302, e.g. shown in FIG. 8, within the receptacle containing the assay reagents that can measure the time of arrival of the fluid containing the target. In this way, the precise incubation time of the target with the assay reagents before magnetic label detection can be determined. For assays in which the assay reactions occur on the surface of detection surface 4, the fluid detector should be in the first receptacle 1, whereas in assays with reactions on the magnetic label 5, the fluid detector should be placed in the second receptacle 2. The incubation time is the time between fluid arrival and the transport of the magnetic labels 5 out of the second receptacle 2. If there is a step between the fluid arrival and the transport of the magnetic labels that removes assay reagents, then the incubation time is the time between the fluid arrival and the reagent removal. The fluid detector can employ electrical (e.g. impedance) or optical or acoustic/sonic techniques to determine the arrival of the fluid. Magnetic detection (e.g. bulk sensitive GMR, Hall sensor, magnetic coils etc.) can be used in the second receptacle 2 to determine the dissolution and displacement of the magnetic labels 5 from the surface by the arrival of the fluid.

Figure 9:
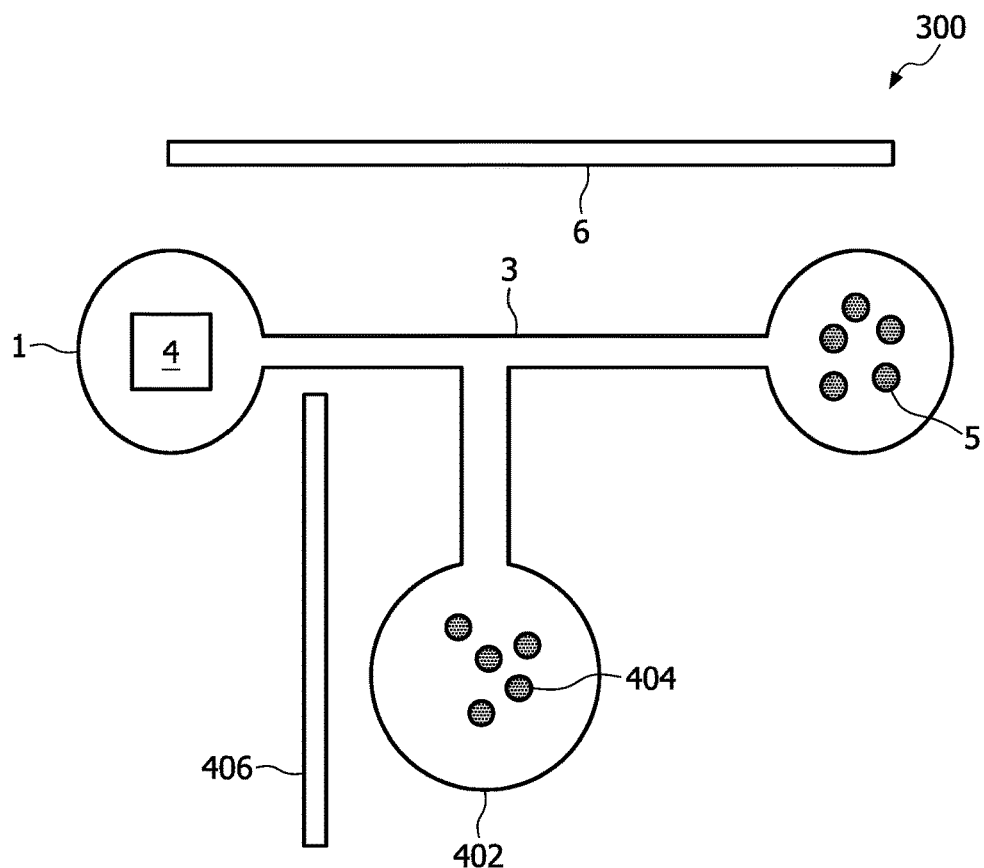
FIG. 9 is a schematic representation of a detection device component adapted for providing label-magnification according to a particular embodiment of the first aspect of the present invention.

In an eighth particular embodiment, the detection system 100 of the present invention can also be used in conjunction with signal amplification through the addition of a secondary magnetic label. The primary labelling step can be separated in time from the secondary labelling step by the addition of a further receptacle connected to the interconnection channel 3 between the first receptacle 1 and the second receptacle 3 containing the secondary magnetic labels. After the assay reaction has occurred and the primary labels are brought to the detection surface 4 for detection with a magnetic force, the secondary magnetic labels are transported from their further receptacle to the first receptacle with a further magnetic field generator, i.e. using a magnetic force. There they have the ability to bind to the primary magnetic label and can be detected. It is desirable to remove primary magnetic labels that are not bound to the detection surface 4 with a magnetic force and e.g. transport them for example back to the second receptacle 2, before the secondary magnetic label is transported to the first receptacle 1. In this way the secondary labels only bind to primary magnetic labels attached to the detection surface 4. An exemplary detection system is shown in FIG. 9, showing the further receptacle 402, the secondary magnetic labels 404 and the further magnetic field generator 406, adapted for actively transporting the secondary magnetic labels 404.

Figure 10A:
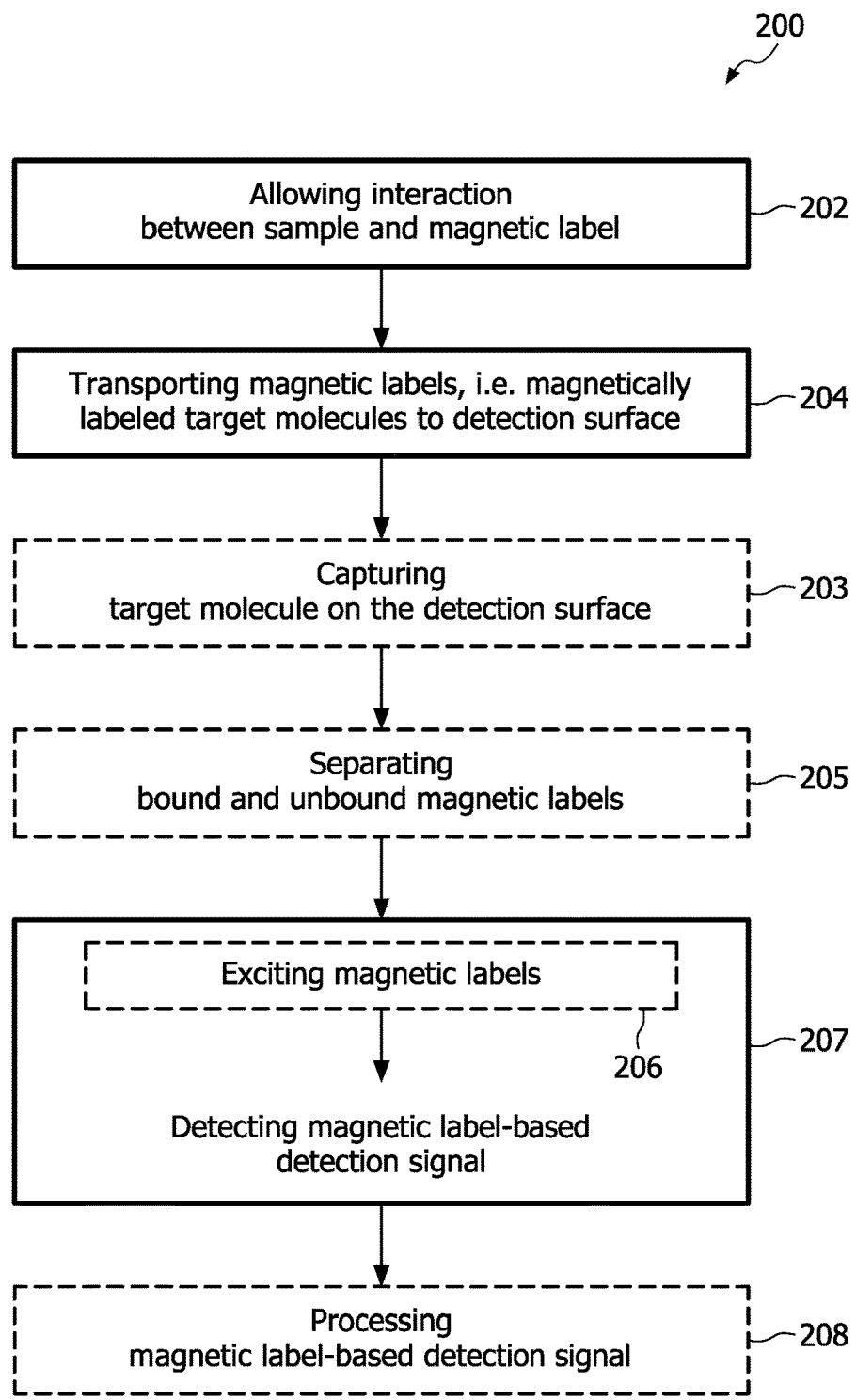
FIG. 10a and FIG. 10b are flow diagrams of methods for detecting target molecules in a sample according to a second aspect of the present invention.
Figure 10B:
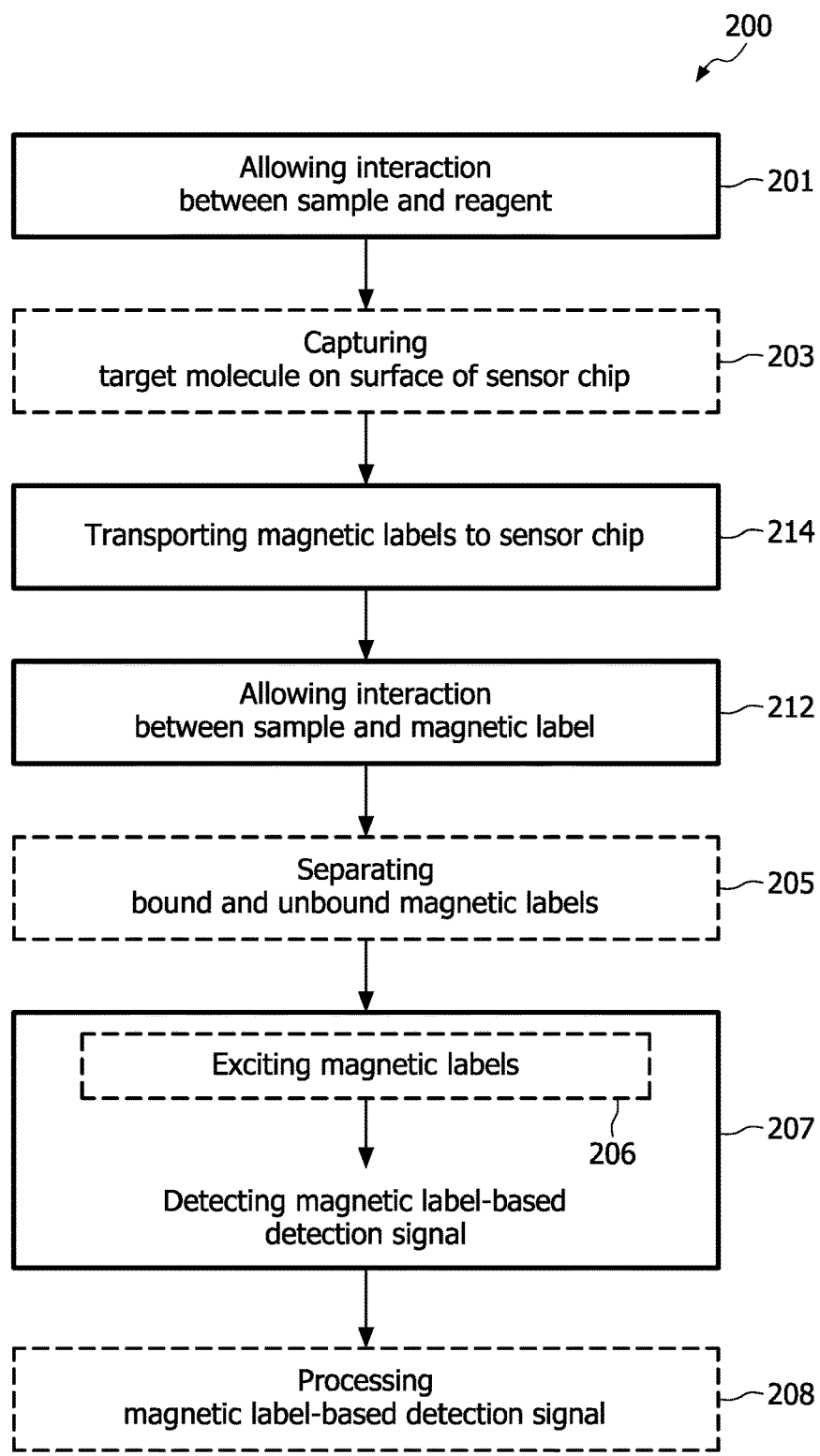

According to a second aspect, the present invention provides a detection method for detecting at least one target molecule in a sample. The latter preferably also may allow to quantify target molecules in a sample. Such a method for detecting a target typically comprises allowing interaction between the sample and at least one magnetic label to thereby obtain at least one magnetically labelled target molecule, and transporting magnetic labels to a detection surface. Transport of the at least one magnetic label thereby may occur prior to or after interaction of the at least one magnetic label with the sample. The method furthermore comprises detecting a magnetic label assisted detection signal. Exemplary methods for detecting at least one target molecule in a sample according to the present aspect is illustrated by way of example in FIG. 10*a* and FIG. 10*b*. Standard and optional features of the method 200 will be described using the flow diagram shown in FIG. 10*a* and FIG. 10*b*, indicating standard and optional steps of an exemplary detection method.

One step of the detection method 200 comprises allowing interaction 202, 212 of the sample and at least one magnetic label, resulting in at least one magnetically labelled target molecule. This may comprise introducing sample fluid, e.g. a drop of sample fluid, in one of the receptacles of the detection system e.g. by gravitational or capillary force. Alternatively, the sample fluid also may be actively or passively pumped towards the receptacles of the device. Allowing interaction between a sample and at least one magnetic label may thus comprise controlling a sample providing means. Allowing interaction between a sample and a magnetic label may also comprise facilitating the interaction by e.g. a magnetic actuator. Allowing interaction thus results in a magnetically labelled target molecule.

In another step, the method 200 comprises transporting 204, 214 the magnetic labels to a detection surface. Transporting 204, 214 the magnetic labels may comprise transporting the magnetic labels from one receptacle to another receptacle comprising the detection surface. Depending on whether allowing interaction between the sample and the magnetic label has already occurred the magnetic labels transported may at the moment of transport already be connected to the target molecule or not.

Allowing interaction 202, 212 of the sample and at least one magnetic label and transporting 204, 214 the magnetic labels may be performed according to different sequences, i.e. the allowing interaction 202 between the sample and the at least one magnetic label may be performed prior to the transporting 204 as well as the transporting 214 may be performed prior to the allowing interaction 212 between the sample and the at least one magnetic label. The latter will be illustrated by way of two particular embodiments. In one embodiment, steps thereof being illustrated in FIG. 10*a*, the method 200 comprises allowing interaction 202 between the sample, reagent and the at least one magnetic label in one receptacle and then transporting 204 the magnetically labelled target molecule, comprising the magnetic label, e.g. through an interconnection channel, to another receptacle where the detection surface is positioned. The latter is advantageous as unreacted reagents are not interfering with the label-assisted detection step. In a second embodiment, the method 200 comprises allowing reagents and sample to interact 201 in one receptacle, transporting 214 the at least one magnetic label from a first receptacle to the receptacle wherein interaction between the reagents and the sample has occurred, e.g. after a predetermined interaction time for the sample and the reagents, and allowing interaction 212 between the sample and the at least one magnetic label.

Another optional step preferably occurring in the detection method 200 is capturing 203 of the target molecule on the detection surface 4. The latter may e.g. be performed by binding of the target molecule or reagent components bound thereon to the detection surface or to biologically or biochemically active moieties thereon. The latter may be performed after interaction 202 of the at least one magnetic label with the at least one target molecule, i.e. after transport 204 of the magnetically labelled target, or prior to interaction of the at least one magnetic label with the at least one target molecule, i.e. prior to transporting 214 of the magnetic label.

In a further step, after the allowing interaction 202, 212 between the magnetic label and the at least one target molecule and the transporting magnetic labels 204, 214, detecting 207 of a magnetic label assisted detection signal may be performed. It may be performed using any suitable detection method in accordance with the chosen magnetic labels. Envisaged suitable detection methods include optical detection mechanisms such as, but not limited to, fluorescence detection, SERRS and detection of absorption and/or scattering signals, electrical signal detection (e.g. impedance), mass detection, acoustic/sonic detection, and magnetic detection methods, e.g. using a Hall sensor, a GMR, TMR or AMR. Detecting can be done by measurement of a direct property of the magnetic label or it can be done by measurement of a property resulting from the modification of the label, i.e. for example by attachment of a second label such as a enzymatic label like peroxidase, phosphatase or oxidase, an electrochemical label or a fluorescence label like a core shell magnetic label in which the core contains the magnetic species and the shell has a fluorescent dye or vice versa. In a particular embodiment, the method furthermore may comprise exciting 206 the magnetic labels allowing to generate a magnetic label-assisted signal to be detected. Depending on the type of magnetic labels used, such exciting may for example be irradiating the sample for inducing luminescence or providing an electromagnetic field to the sample for inducing an orientation of the magnetic labels, etc.

The detection method 200 for detecting and/or quantifying may furthermore comprise the step of processing 208 the magnetic label-assisted detection signal. The processing may comprise obtaining a qualitative, or more preferably, a quantitative result from the magnetic label-assisted detection signal. The processing may be based on using predetermined algorithms, using neural networks or in any other suitable way. It may be done in an automatic and/or automated way.

In one embodiment, prior to the detection step, an optional separating step 205 may be performed for separating unbound or weakly bound magnetic labels from bound magnetic labels. The latter may be advantageous to obtain more accurate measurements as it avoids influencing of the detection result by unbound or weakly bound magnetic labels. The removal of unbound or weakly bound magnetic labels may be ensured by separating and removing unbound or weakly bound magnetic labels from the bound magnetic labels, bound to the detection surface via a capture probe or a tag. The latter may be performed by applying a physical or chemical force such as a flow field, acoustic field, gravitational force, electromagnetic field to move and/or remove the unbound magnetic labels. Exemplary separating techniques include rinsing, sedimentation, precipitation, centrifugation, sonication, application of magnetic and/or electric fields and field gradients.

The detection method 200 may also include a calibration step. Therefore, the sensor signal may be measured before and after wetting so as to calibrate the sensitivity of the sensor chip to the magnetic label. Such a calibration step may be performed or processed using predetermined algorithms and the results of such a calibration step may be taken into account in the signal processing step, e.g. during quantifying of the detection results. The calibration may be a calibration for specific magnetic label-sensitivity. The detection method 200 according to the present invention may be combined with magnetic extraction and a catch assay in which a solution is pre-incubated with magnetic particles or magnetisable particles.

In a third aspect, the present invention relates to a sensor component for use in a detection system according to the first aspect of the present invention. The sensor component typically comprises a first receptacle comprising a detection surface and without label, at least prior to use, i.e. prior to interaction between the sample an the label, a second receptacle comprising at least one magnetic label, at least prior to use, whereby the magnetic label is adapted for interacting with at least one target molecule to be detected. The sensor component furthermore is adapted for enabling transport of the at least one magnetic label from the at least a second receptacle to the at least a first receptacle, using a magnetic field. Other features of the first receptacle, the second receptacle, an interconnection channel, supply and/or removal channels and/or supply and/or removal receptacles and components comprises therein may be the same and have the same features and advantages as described in the first aspect of the invention. The detector for label-assisted detecting at the detection surface as well as the magnetic field generator may be completely or partially external to or part of the sensor component. The detector for label-assisted detecting as well as the magnetic field generator may be static with respect to the sensor component or may be scanning. The sensor component may be disposable. It may be referred to as the sensor chip. The sensor component may be a part of the detection system as described above. The sensor component 300 may comprise an amount, e.g. predetermined amount, of at least one target molecule in a buffer solution. The latter may serve as a positive control and/or as a standard. The selected at least one target molecule in buffer solution typically will depend on the type of assay to be performed with the sensor chip 4. Optionally the device can be presented as a kit of parts further comprising other components such as a predetermined amount of control fluid allowing for performing a negative control measurement, whereby the sensor chip specifically needs to provide a negative detection signal, indicating the absence of the target molecule tested for.

Other arrangements for accomplishing the objectives of the detection system using transportable magnetic labels embodying the invention will be obvious for those skilled in the art. It is to be understood that although preferred embodiments, specific constructions and configurations, as well as materials, have been discussed herein for devices according to the present invention, various changes or modifications in form and detail may be made without departing from the scope and spirit of this invention.

The invention claimed is:

1. A method for detecting at least one target molecule, the method comprising:
    allowing interaction between a sample containing at least one target molecule and at least one primary magnetic and/or electric label to thereby obtain at least one labeled target molecule,
    applying a first magnetic field having a first orientation to transport the at least one primary magnetic and/or electric labeled target molecule to a detection surface wherein the primary magnetic and/or electric labeled target molecule binds the detection surface,
    applying a second magnetic field having a second orientation to transport at least one secondary magnetic and/or electric label to the detection surface,
    allowing the at least one secondary magnetic and/or electric label to interact with the at least one primary magnetic or electric label to obtain at least one primary and secondary magnetic and/or electric labeled target module,
    after said allowing of said interaction of the primary magnetic and/or electric labeled target molecule, detecting the at least one primary and secondary magnetic and/or electric label bound to the detection surface.

2. The method of claim 1, wherein the magnetic and/or electric label is a magnetic label.

3. The method according to claim 1, wherein the first and second orientations are substantially orthogonal to each other.

4. The method according to claim 1, wherein the first magnetic field transports the primary magnetic and/or electric label along the first orientation without transporting the secondary magnetic and/or electric label, and
    the second magnetic field transports the secondary magnetic and/or electric label along a second orientation without transporting the primary magnetic and/or electric label.

5. The method according to claim 1, further including:
    waiting until the primary magnetic and/or electric label is bound to the detector surface and then applying the first magnetic field again in a manner to transport unbound primary magnetic and/or electric labels out of the first receptacle.

6. The method of claim 1, wherein the detection surface is disposed in a first receptacle, the primary magnetic and/or electric label is contained in a second receptacle, and the secondary magnetic and/or electric label is contained in a third receptacle.

7. The method of claim 6, wherein the sample interacts with the primary magnetic and/or electric label in the first receptacle, and after a predetermined time, the secondary magnetic and/or electric label is transported to the first receptacle to react with the primary magnetic and/or electric label.

8. The method of claim 6, wherein the sample interacts with a reagent and the secondary magnetic and/or electric label in the second receptacle.

9. The method of claim 6, further comprising detecting a time of arrival in the first receptacle of a fluid containing the at least one target molecule.

* * * * *